(12) United States Patent
Nygaard

(10) Patent No.: US 11,273,027 B2
(45) Date of Patent: Mar. 15, 2022

(54) DEVICE AND METHOD FOR AN IMPLANT

(71) Applicant: Carla J. Nygaard, Hastings, MN (US)

(72) Inventor: Carla J. Nygaard, Hastings, MN (US)

(*) Notice: Subject to any disclaimer, the term of this patent is extended or adjusted under 35 U.S.C. 154(b) by 120 days.

(21) Appl. No.: 16/785,030

(22) Filed: Feb. 7, 2020

(65) Prior Publication Data
US 2020/0253717 A1 Aug. 13, 2020

Related U.S. Application Data

(60) Provisional application No. 62/803,316, filed on Feb. 8, 2019.

(51) Int. Cl.
*A61F 2/12* (2006.01)

(52) U.S. Cl.
CPC ........ *A61F 2/12* (2013.01); *A61F 2250/0013* (2013.01); *A61F 2250/0048* (2013.01)

(58) Field of Classification Search
CPC ................ A61F 2/12; A61F 2250/0013; A61F 2250/0048

USPC .......................................... 623/7–8
See application file for complete search history.

(56) References Cited

U.S. PATENT DOCUMENTS

| | | | | |
|---|---|---|---|---|
| 9,399,122 B2* | 7/2016 | Mosharrafa | ............... | A61F 2/12 |
| 9,980,781 B2* | 5/2018 | Leedy | .................... | A61B 90/06 |
| 11,065,075 B2* | 7/2021 | Mosharrafa | ............ | A61B 90/02 |
| 2007/0185575 A1* | 8/2007 | Purkait | ..................... | A61F 2/12 |
| | | | | 623/8 |
| 2007/0233273 A1* | 10/2007 | Connell | .................... | A61F 2/12 |
| | | | | 623/23.72 |
| 2012/0101575 A1* | 4/2012 | Horne | ....................... | A61F 2/12 |
| | | | | 623/8 |
| 2015/0025563 A1* | 1/2015 | Mosharrafa | ............ | A61B 90/02 |
| | | | | 606/191 |

* cited by examiner

*Primary Examiner* — Suzette J Gherbi

(74) *Attorney, Agent, or Firm* — Winthrop & Weinstine, P.A.; Alicia Griffin Mills

(57) ABSTRACT

A novel and advantageous implant device and methods for implanting the device are provided. Particularly, novel and advantageous devices and methods for breast reconstruction are provided. More particularly, novel and advantageous devices and methods for breast reconstruction to provide a more realistic form are provided.

18 Claims, 12 Drawing Sheets

DEVICE AND METHOD FOR AN IMPLANT

CROSS-REFERENCE TO RELATED APPLICATIONS

The present disclosure claims priority to Provisional Application No. 62/803,316, entitled Device and Method for an Implant, and filed Feb. 8, 2019, the content of which is hereby incorporated by reference herein in its entirety.

FIELD OF THE INVENTION

The present disclosure relates to novel and advantageous implant device and methods for implanting the device. Particularly, the present disclosure relates to novel and advantageous devices and methods for breast reconstruction. More particularly, the present disclosure relates to novel and advantageous devices and methods for breast reconstruction to provide a more realistic form.

BACKGROUND OF THE INVENTION

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

FIG. 1 illustrates a side cross sectional view of healthy breast 10. The interior of the breast 10 includes adipose tissue or fat 12, lodes 14, ducts 16. The exterior of the breast includes a nipple 20 and areola 22. The breast is adjacent the pectoral muscle 24, which sits in front of ribs 26. FIG. 2 illustrates a side view of a healthy breast 10, showing the nipple 20 and the areola 22. As shown, the nipple 20 is raised and has a different curvature C than the rest of the breast. FIGS. 3a through 3c illustrate common nipple profiles. FIG. 3a illustrates a regular nipple 20a profile. FIG. 3b illustrates a flat nipple 20b profile. FIG. 3c illustrates an inverted nipple 20c profile.

A mastectomy is surgery to remove all breast tissue from a breast as a way to treat or prevent breast cancer. This involves removal of the adipose tissue 12, lodes 14, and ducts 16. Most commonly, the nipple 20 and areola 22 are removed during the mastectomy to lower the chance of cancer returning. Breast reconstruction is commonly performed after mastectomy and may include implants, tissue flap procedures, or other. Sometimes, removing a breast tumor does not leave enough skin to create a breast and tissue expansion is done before a breast implant is implanted.

A reconstructed breast is not necessarily provided with a nipple. When nipple reconstruction is done, it is typically done after breast reconstruction is complete. Various options exist for nipple reconstruction. Surgeons can make a nipple from tissue taken from the back or abdominal flap. It is then tattooed to resemble the color of a nipple. In rare cases, the nipple from the original breast can be reattached, but only if the surgeon is convinced the tissue is cancer-free. Another option is a prosthetic nipple. This involves a plastic surgeon making a copy of the natural nipple and coloring the areola. It is glued to the breast and reglued every week or so.

Thus, there is a need in the art for a device and method for breast reconstruction with nipple reconstruction to provide a more realistic form.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure, in one or more embodiments, relates to a system for breast reconstruction. The system includes an expansion implant and a reconstruction implant. The expansion implant includes an expander portion and a nub. The expander portion may be configured to receive a fluid and expand upon receiving the fluid. The nub may comprise a substantially rigid protrusion and may extend outwardly from the expander portion when the expander is in an expanded configuration. The reconstruction implant may comprise a breast portion and a nipple portion extending outwardly from the breast portion. The nub may emulate a human nipple. The expansion implant may include a valve for accessing an interior of the expander portion. The expander portion may have a round shape.

In another embodiment, an expansion implant is provided. The expansion implant may have an expander portion and a nub. The expander portion may be configured to receive a fluid and expand upon receiving the fluid. The nub may comprise a substantially rigid protrusion and may extend outwardly from the expander portion when the expander is in an expanded configuration. The expansion implant may further comprise a port for accessing an interior of the expander portion. The nub may be configured to form a nipple cavity in a breast region of a human when implanted.

In yet a further embodiment, a method for reconstruction of a breast is provided. The method may comprise implanting an expansion implant into a breast region, expanding expansion implant to form a cavity, removing the expansion implant, and implanting a reconstruction implant into the cavity. The cavity created in the breast region may include a nipple cavity and implanting the reconstruction implant in the cavity may include positioning a nipple portion of the reconstruction implant into the nipple cavity.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

The present disclosure relates to novel and advantageous implant device and methods for implanting the device. Particularly, the present disclosure relates to novel and advantageous devices and methods for breast reconstruction. More particularly, the present disclosure relates to novel and advantageous devices and methods for breast reconstruction to provide a more realistic form.

In various embodiments, an expansion implant and a reconstruction implant may be provided. The expansion implant is provided having an expander portion and a nub. The expander portion may be filled with a biocompatible fluid for stretching the skin proximate the implant as implanted. The nub may be a substantially rigid protrusion positioned to visibly extend from the expander portion to have an effect of mimicking a nipple after the implant is implanted. After removal of the expansion implant, a nipple like protrusion is present protruding from the breast mound. The reconstruction implant may have a breast portion and a protrusion, the breast portion acting to reconstruct the breast tissue and the protrusion acting to reconstruct the nipple. Accordingly, the reconstruction implant may be placed in the breast mound, with a protrusion aligning with the nipple like protrusion.

After a mastectomy, breast reconstruction may be done. Commonly, after the mastectomy, there is insufficient skin to create a breast. In this situation, expansion of the breast skin and muscle may be done using a temporary tissue expander.

Figure 1:
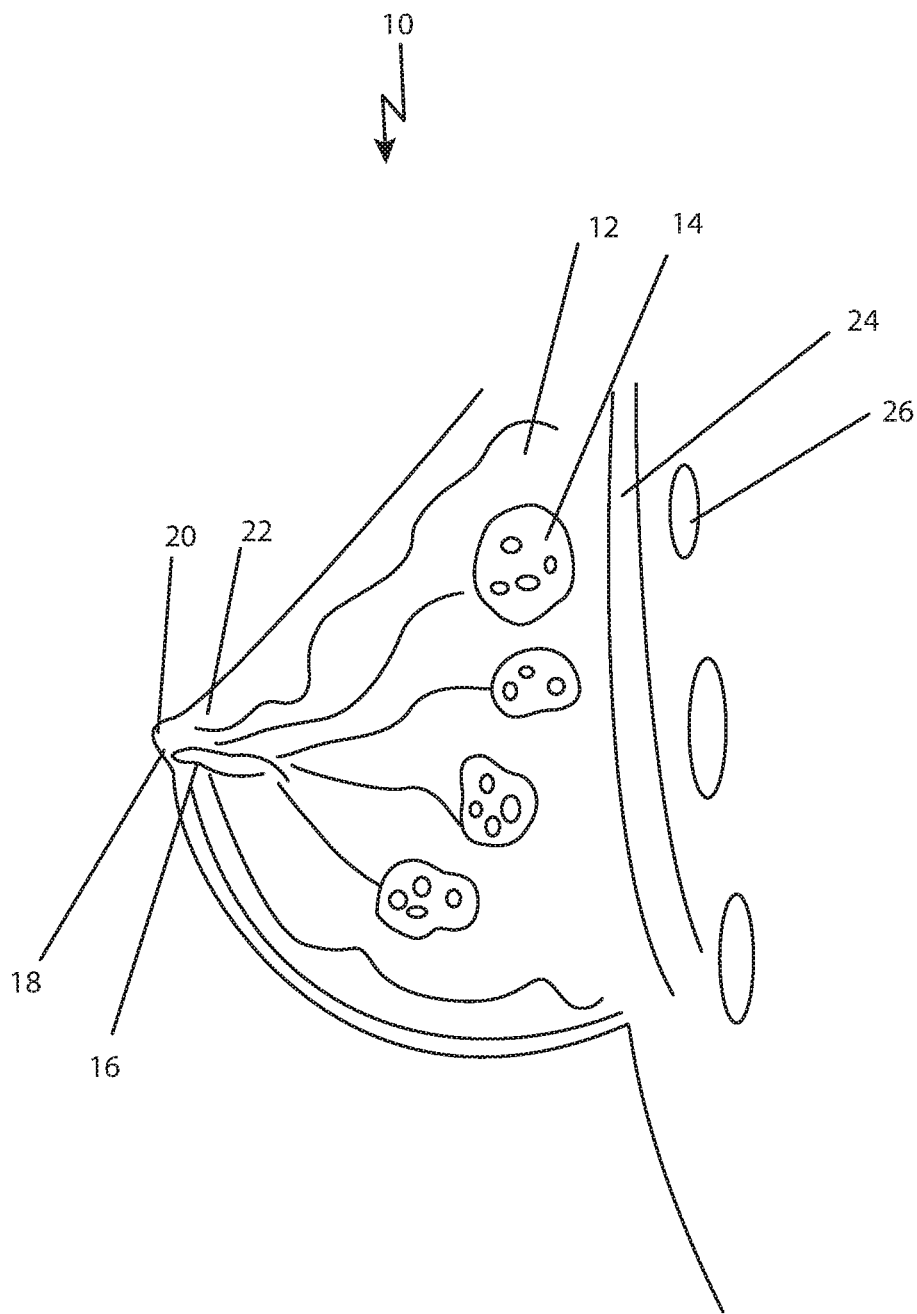
FIG. 1 illustrates a side cross sectional view of healthy breast.
Figure 2:
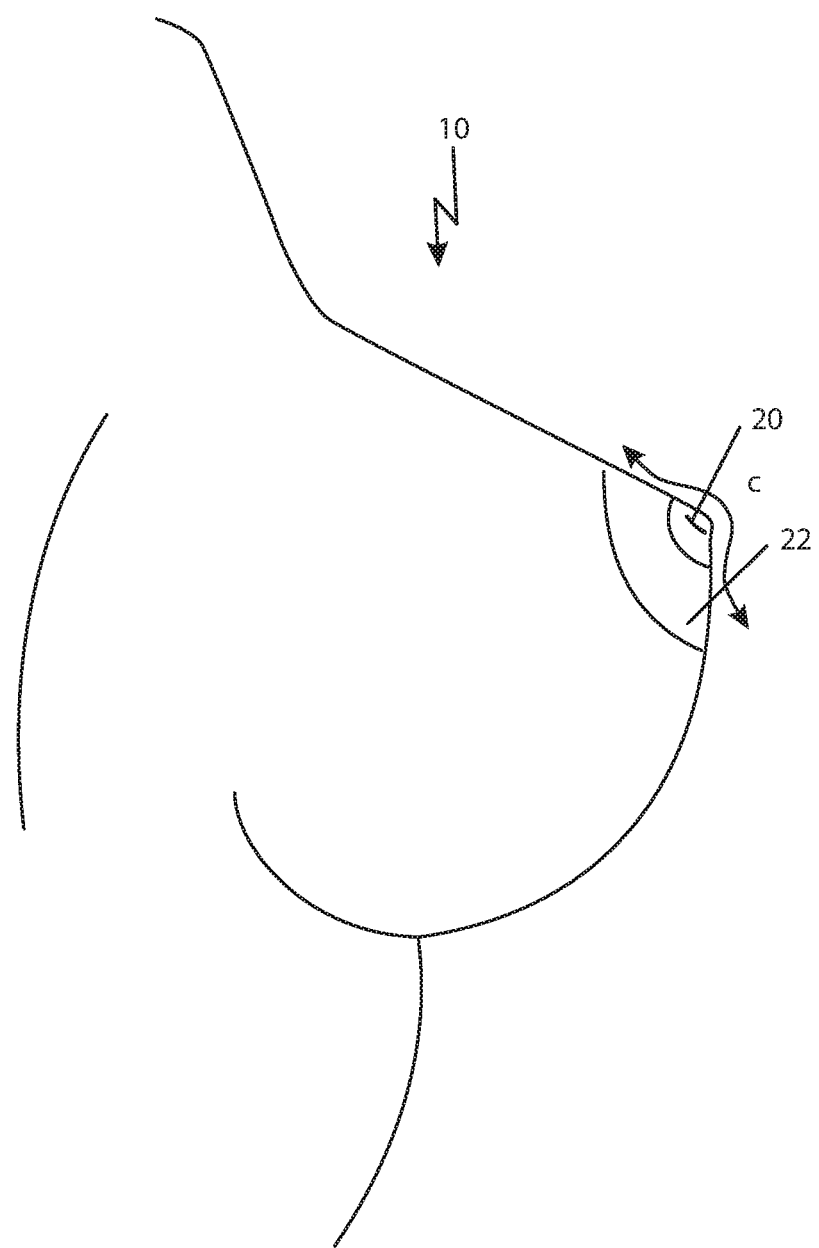
FIG. 2 illustrates a side view of a healthy breast, showing the nipple and the areola.
Figure 3A:
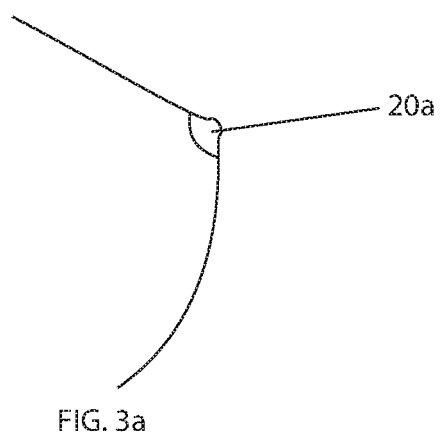
FIG. 3a illustrates a regular nipple profile.
Figure 3B:
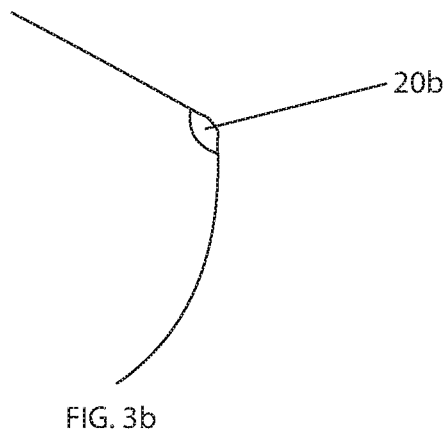
FIG. 3b illustrates a flat nipple profile.
Figure 3C:
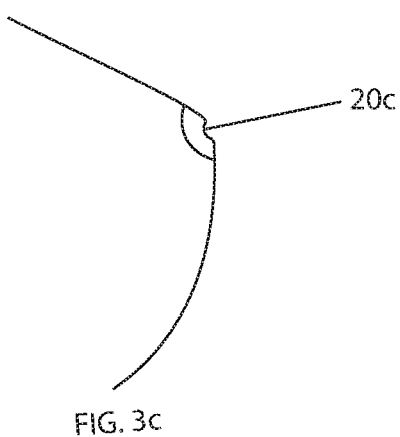
FIG. 3c illustrates an inverted nipple profile.
Figure 4:
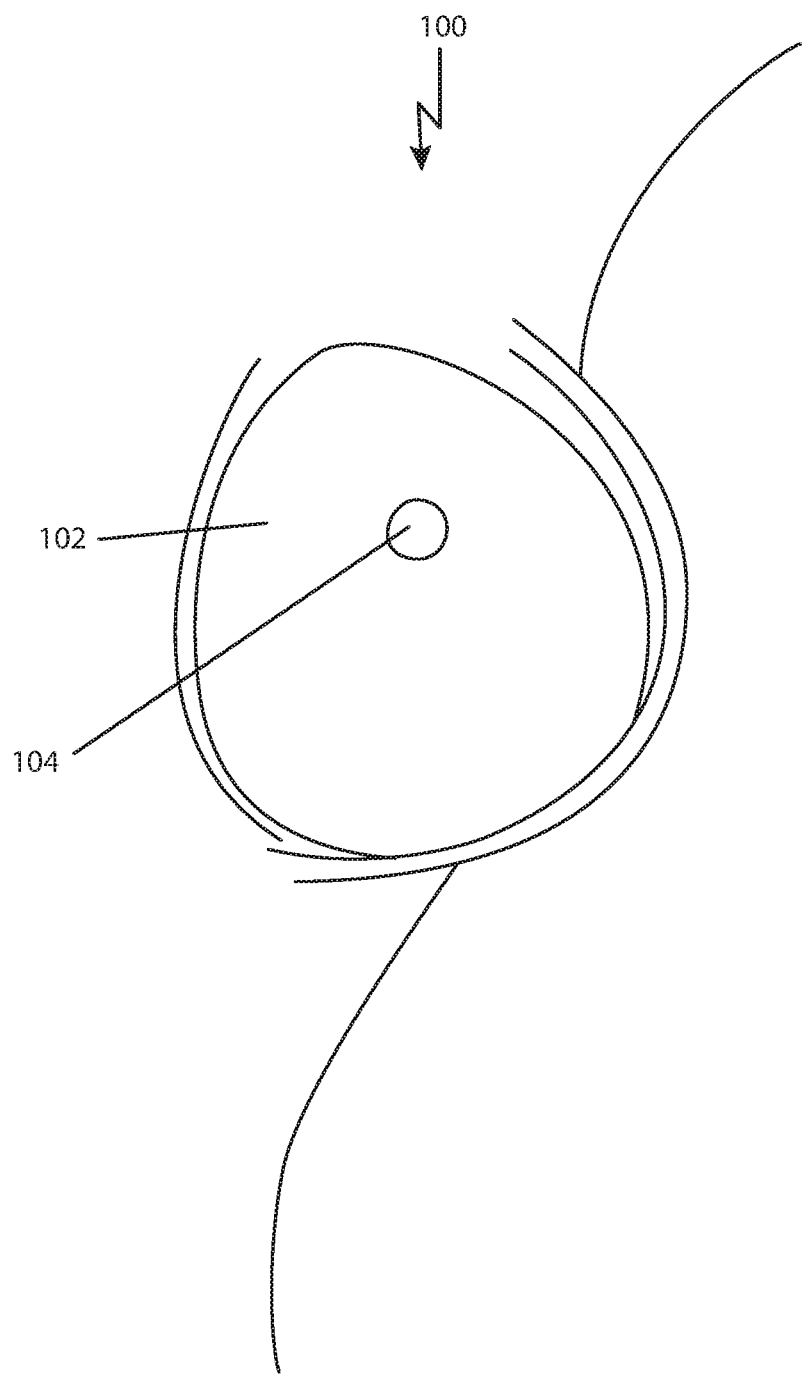
FIG. 4 illustrates a front view of an expansion implant as implanted, in accordance with one embodiment.

FIG. 4 illustrates a front view an expansion implant as implanted in the body, in accordance with one embodiment. In the embodiment shown, the expansion implant 100 includes an expander portion 102 and a nub or protrusion 104. The expander portion 100 may comprise a shell that may filled with a biocompatible fluid to expand the shell. In various embodiments, the shell may comprise silicone or other medical grade material and the biocompatible fluid may comprise saline, silicon, or other biocompatible medical grade material. The expander portion may be any suitable shape. In one embodiment, the expander portion, as expanded, is round. In another embodiment, the expander portion, as expanded, is anatomically shaped. For example, the expander portion may have a teardrop shape, may have a conical shape, may have an oval base, may have a low profile or may have a high profile, or have other suitable configuration. The nub 104 is sized to mimic the extension of a nipple from the breast tissue. The nub 104 may be formed from, for example, silicone. In some embodiments, the nub 104 may be integral with the expander portion 102 and comprise a thicker portion of the silicone material used to form the expander portion 102. In other embodiments, the nub 104 may comprise a separate component that is coupled to the expander portion 102.

In some embodiments, the nub 104 may not extend outwardly from the expander portion 102 unless and/or until the expander portion 102 is filled or partially filled with the biocompatible fluid. Thus, while the nub 104 may be positioned to visibly extend from the expander portion 102 when the expansion implant 100 is implanted and the expander portion 102 expanded, the nub 104 may not visibly extend from an outside surface of the expander portion 102 when the expander portion is empty and/or is only partially filled with a biocompatible fluid. In such an embodiment, when the expander portion 102 is at least partially filled with the biocompatible fluid, the nub 104 may pop up and outwardly from the expander portion 102. Alternatively, the implant may be configured such that the nub may pop up and outwardly from the expander portion only when the expander portion is fully filled or filled to its pre-determined maximum capacity with a pre-determined amount of biocompatible fluid.

Figure 5:
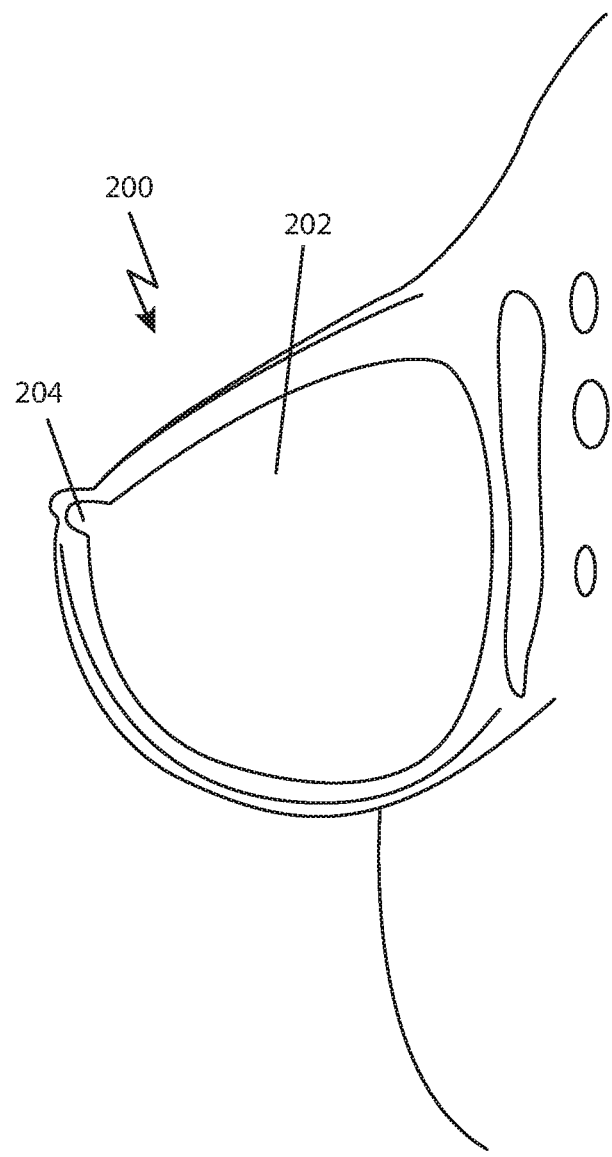
FIG. 5 illustrates a side cross sectional view of a human with a reconstruction implant implanted, in accordance with one embodiment.

FIG. 5 illustrates a side cross sectional view of a reconstruction implant 200 as implanted in the body, in accordance with one embodiment. The reconstruction implant may comprise a breast portion 202 and a protrusion or nipple portion 204.

Figure 6:
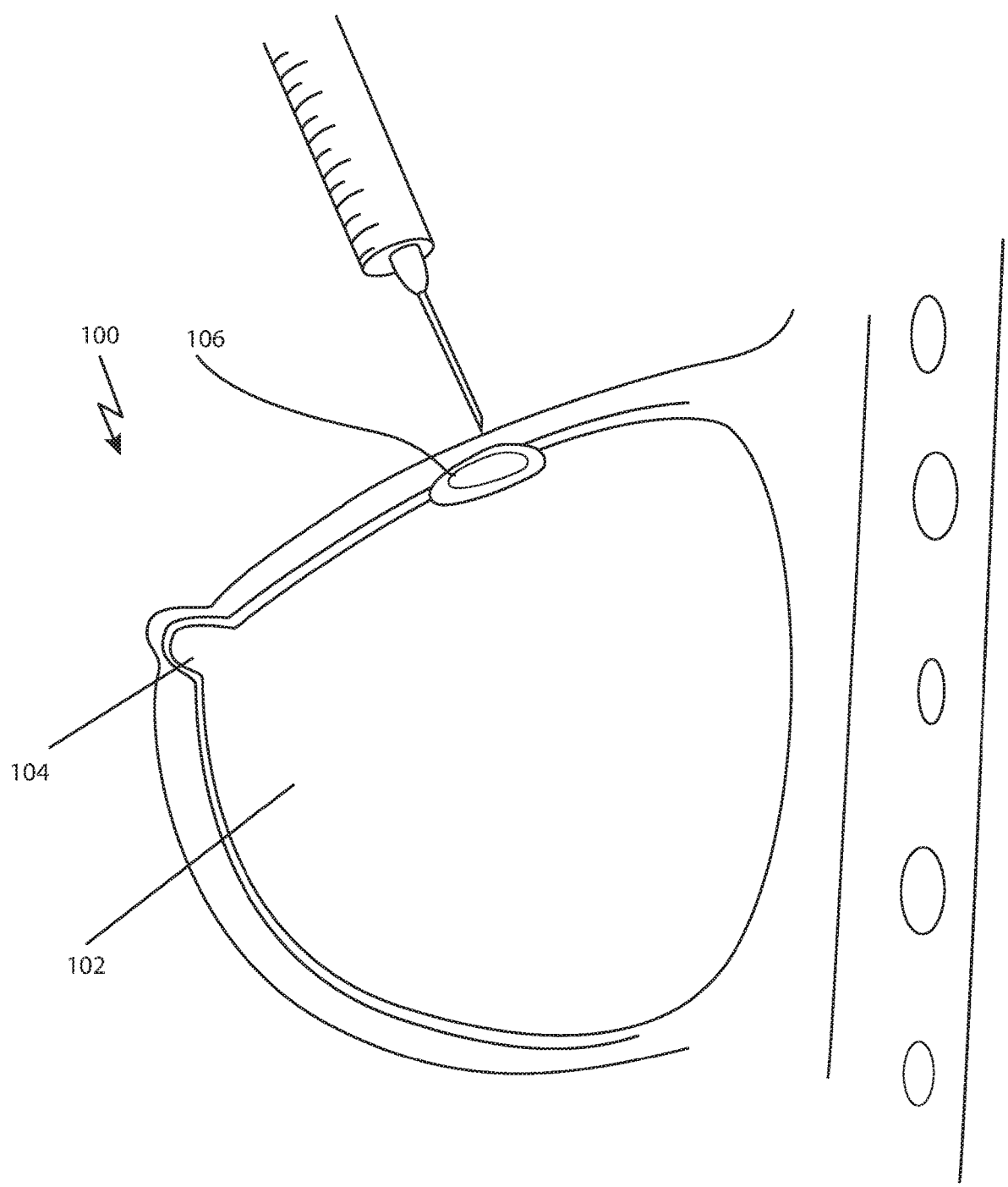
FIG. 6 illustrates an expansion implant having a valve or port, in accordance with one embodiment.

FIG. 6 illustrates an expansion implant having a valve or port, in accordance with one embodiment. As shown, the expansion implant 100 may be provided with a port or valve 106 accessing the interior of the expander portion 102. The port or valve 106 may be positioned on any outwardly (away from the patient's body) facing surface of the expansion implant that does not interfere with the nub 104. The biocompatible fluid, such as saline, is injected to the interior of the expander portion through the port or valve 106. It is to be appreciated that any expansion implant shown and described herein may have a port for accessing the interior of the expander portion, regardless of whether shown.

The expansion implant 100 may be used to expand skin in the breast area to make room for insertion of a reconstruction implant. The expansion implant 100 is placed in front of the pectoralis muscle. This may be done during a mastectomy or at a point thereafter. In general, after the expansion implant 100 is implanted, the expansion implant 100 is gradually filled with a biocompatible fluid such as saline through the port or valve 106. As it expands, the expansion implant 100 stretches skin in the breast area until a desired size of breast mound is achieved. After the skin has stretched sufficiently to accommodate an implant, the expansion implant 100 may be removed and a reconstruction implant inserted into the pocket created during expansion. In some embodiments, the biocompatible fluid may be partially or entirely drained from the expansion implant prior to removal of the expansion implant.

Figure 7A:
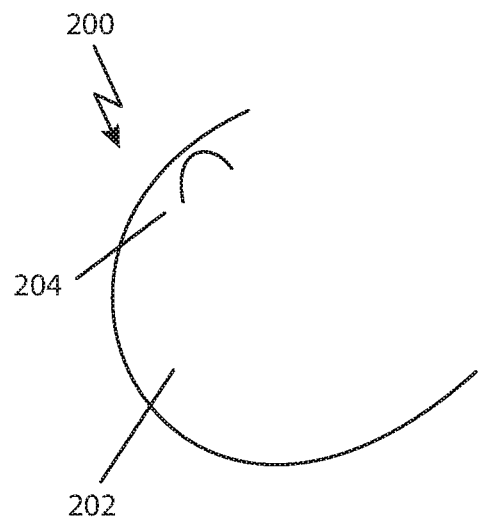
FIG. 7a illustrates a perspective view of reconstruction implant before implantation, in accordance with one embodiment.
Figure 7B:
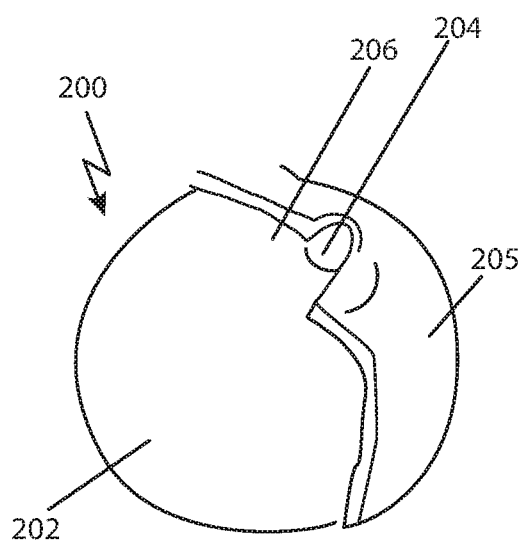
FIG. 7b illustrates a cut away view of a reconstruction implant as implanted, in accordance with one embodiment.
Figure 7C:
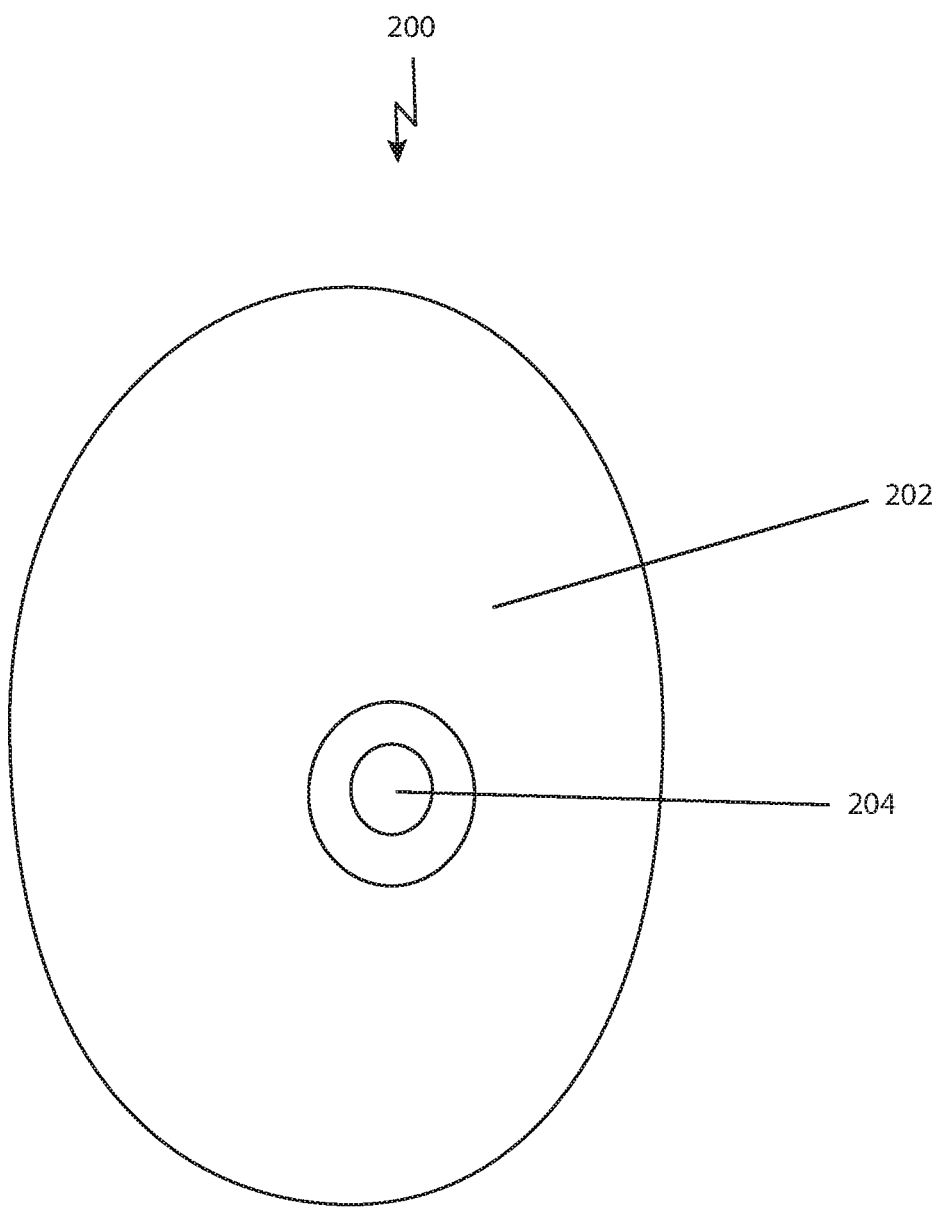
FIG. 7c illustrates a front view of a reconstruction implant before implantation, in accordance with one embodiment.

Returning now to the reconstruction implant, FIGS. 7a-7c illustrate a reconstruction implant 200, in accordance with one embodiment. FIG. 7a illustrates a perspective view of reconstruction implant 200 before implantation. FIG. 7b illustrates a cut away view of a reconstruction implant 200 as implanted under the skin 205 of a patient. As shown, the skin 205 extends over the nipple portion 204 such that the reconstructed breast has a three dimensional nipple reconstruction. FIG. 7c illustrates a front view of a reconstruction implant 200 before implantation. As shown, the reconstruction implant 200 includes a breast portion 202 and a protrusion or nipple portion 204. The nipple portion 204 extends outwardly from the outward facing surface 206. In some embodiments, the outward facing surface may be textured to facilitate breast tissue adherence to the reconstruction implant 200. In other embodiments, all surfaces of the reconstruction implant may be smooth.

In one embodiment, the breast portion 202, as expanded, is round. In another embodiment, the breast portion 202, as expanded, is anatomically shaped. For example, the breast portion 202 may have a teardrop shape, may have a conical shape, may have an oval base, may have a low profile or may have a high profile, or have other suitable configuration.

Figure 8C:
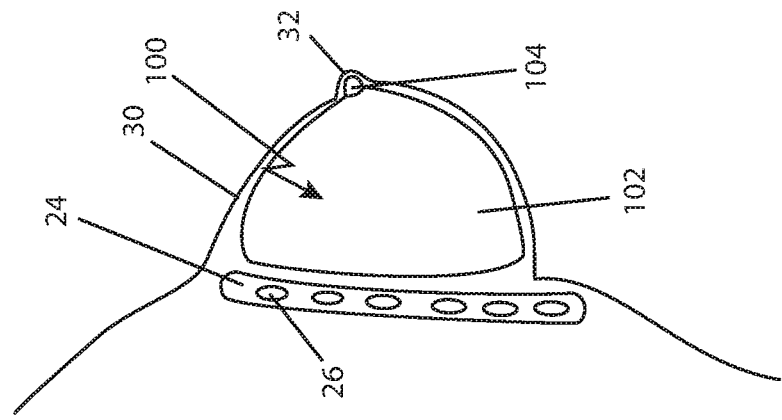
FIG. 8c illustrates the expansion implant of FIG. 8a as implanted and fully expanded, in accordance with one embodiment.
Figure 8B:
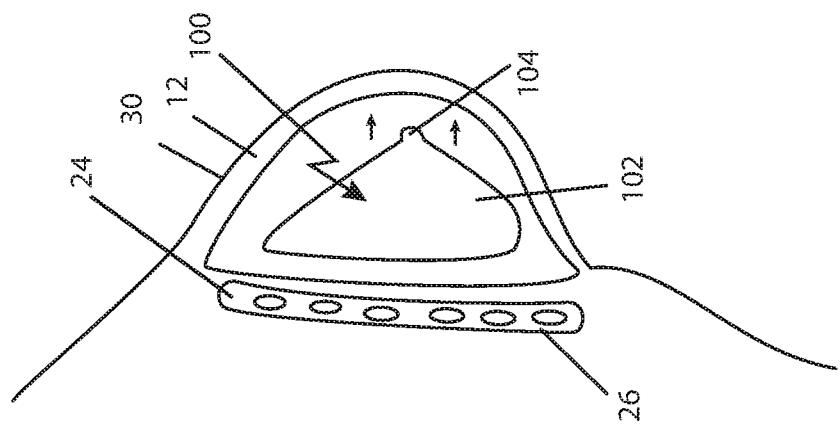
FIG. 8b illustrates the expansion implant of FIG. 8a as implanted and partially expanded, in accordance with one embodiment.
Figure 8A:
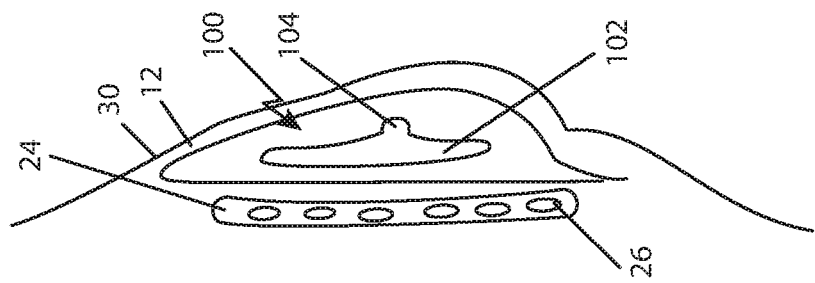
FIG. 8a illustrates an expansion implant as implanted but not expanded, in accordance with one embodiment.

Returning now to expansion of the breast tissue before implanting the reconstruction implant, FIGS. 8a-8c illustrate expansion of the expansion implant 100 after implantation, in accordance with one embodiment. FIG. 8a illustrates the expansion implant 100 as implanted but not expanded. FIG. 8b illustrates the expansion implant 100 as implanted and partially expanded. FIG. 8c illustrates the expansion implant 100 of as implanted and fully expanded. The port is not visible in FIGS. 8a-8c.

The expansion implant 100 is implanted in front of the ribs 26 and pectoral muscle 24 and behind the skin 30 and fatty tissue 12. As shown in FIG. 8a, the initial configuration of the expansion implant 100 is substantially flat. In this configuration, the nub 104 does not press into the skin 30 and does not create a nipple-like protrusion from the breast mound. As shown in FIG. 8b, as the expansion implant 100 is filled with a biocompatible fluid, such as saline, it takes on an expanded configuration. The configuration shown in FIG. 8b is partially expanded. When partially expanded, the expansion implant 100 pushes the skin 30 outwardly but the nub 104 does not yet create a nipple-like protrusion from the breast mound. FIG. 8c illustrates the expansion implant 100 as fully expanded with the nub 104 pressing against skin 30 and creating a nipple-like protrusion 32.

Figure 9B:
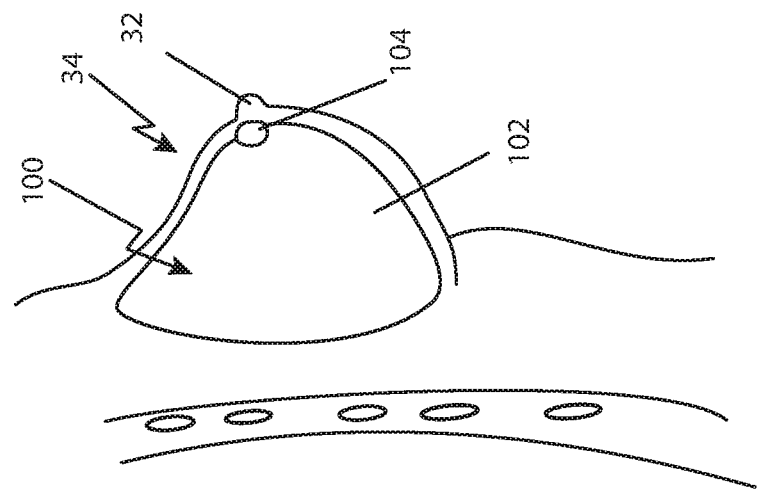
FIG. 9b illustrates a breast mound created with an expansion implant having an expander portion and a nub, in accordance with one embodiment.
Figure 9A:
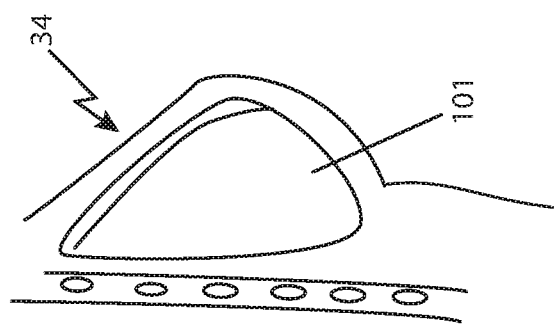
FIG. 9a illustrates a breast mound created with a standard expansion implant.

FIGS. 9a and 9b illustrate the breast mounds 34 created with a standard expansion implant 101 and with a expansion implant 100 having an expander portion 102 and a nub 104, as described herein. FIG. 9a illustrates a breast mound 34 created with a standard expansion implant 101. As shown, the breast mound 34 has a substantially smooth surface. FIG. 9b illustrates a breast mound 34 created with an expansion implant 100 having an expander portion 102 and a nub 104 as taught herein, in accordance with one embodiment. As shown, the breast mound 34 includes a nipple-like protrusion 32.

In general, the expansion implant, including the expander portion and the nub, functions or operates substantially similarly to a mold or a die. Accordingly, as the expander portion is fully or partially filled with the biocompatible fluid, it presses or pushes against at least a portion of the skin, causing the skin to stretch. As the expansion implant fills with biocompatible fluid, the nub pops up and pushes or presses against at least a portion of the skin to form a corresponding protrusion extending outwardly from the body. The pocket around the expansion implant generally takes on the shape of the expansion implant, including both the expander portion and the nub.

Removal of the expansion implant leaves a void or hollow under the skin having a shape, size, and/or form that is substantially similar to that of the expansion implant. The void, and associated expanded skin, includes one or more protrusions extending outwardly from the body, corresponding to the position of the nub while the expansion implant was implanted. The nub of the expansion implant forms a pocket in the breast mound and a nipple like protrusion pocket in the skin over the breast mound. The thus formed pockets have shapes substantially similar to a breast and a nipple.

After the expansion implant has been removed, a reconstruction implant may be placed in the pocket formed by the expansion implant. In general the reconstruction implant may be configured to fill the void or hollow formed by the expander under the skin and may have a shape, size, and/or form substantially similar to that of the stretched skin, or breast mound, formed by the expansion implant. The reconstruction implant may include a breast portion and a nub extending from the breast portion. In some embodiments, the breast portion and the nub be entirely separate components and may be implanted separately.

In some embodiments, the shape, size and/or form of the protrusion of the reconstruction implant is substantially similar to the shape, size and/or form to that of the nub of the expansion implant. Likewise, the location or position of the protrusion of the reconstruction implant corresponds to location or position of the nub of the expansion implant. In other words, the size, shape and/or form of the reconstruction implant and the void or hollow under the skin will be substantially similar to the shape, size and/or form of the expansion implant before the removal procedure is initiated.

During implantation, the reconstruction implant may be oriented such that at least a portion of the protrusion is positioned within a corresponding nipple like protrusion pocket formed by the nub of the expansion implant.

Figure 10A:
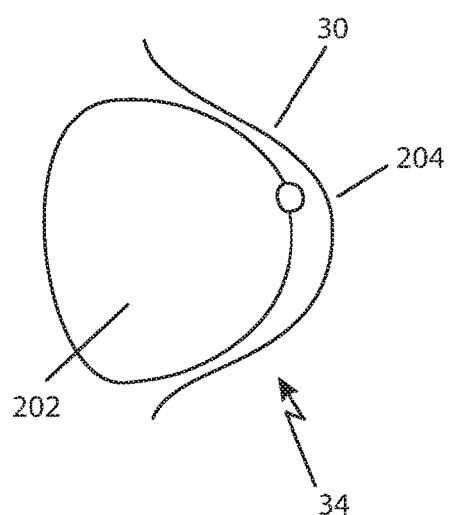
FIG. 10a illustrates a reconstruction implant as initially implanted into the breast mound, in accordance with one embodiment.
Figure 10B:
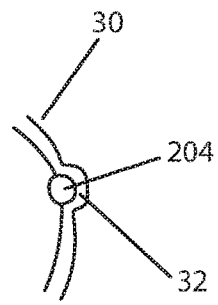
FIG. 10b illustrates skin tightening to the protrusion to form a nipple like protrusion, in accordance with one embodiment.
Figure 10C:
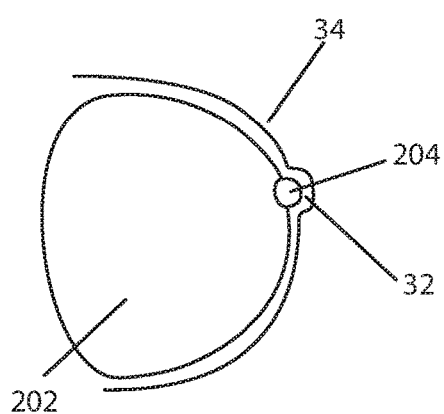
FIG. 10c illustrates a side cross sectional view of a breast with the skin tightened to the protrusion and forming a nipple like protrusion, in accordance with one embodiment.
Figure 10D:
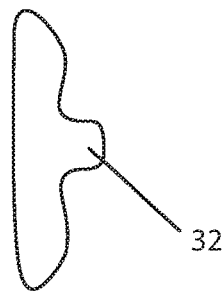
FIG. 10d illustrates a close up of a nipple protrusion, in accordance with one embodiment.

FIGS. 10a-10d illustrate aspects of the reconstruction implant 200 as implanted. FIG. 10a illustrates the reconstruction implant 200 as initially implanted into the breast mound 34. The breast portion 202 fills the created pocket and but does not yet create a nipple like protrusion from the breast mound. As the skin 30 adjusts, it tightens around the protrusion 204 to form a nipple like protrusion 32 from the breast mound 34, shown in FIGS. 10b and 10c. FIG. 10b illustrates skin tightening to the protrusion to form a nipple like protrusion and FIG. 10c illustrates a side cross sectional view of a breast with the skin tightened to the protrusion and forming a nipple like protrusion. FIG. 10d illustrates a close up of the nipple protrusion 32, in accordance with one embodiment.

In general, the reconstruction implant may be at least partially pliable or flexible or supple. In certain embodiments, the implant may be adjusted or repositioned to conform with the shape, size and/or form of the hollow or void under the skin by the expansion implant.

Figure 11B:
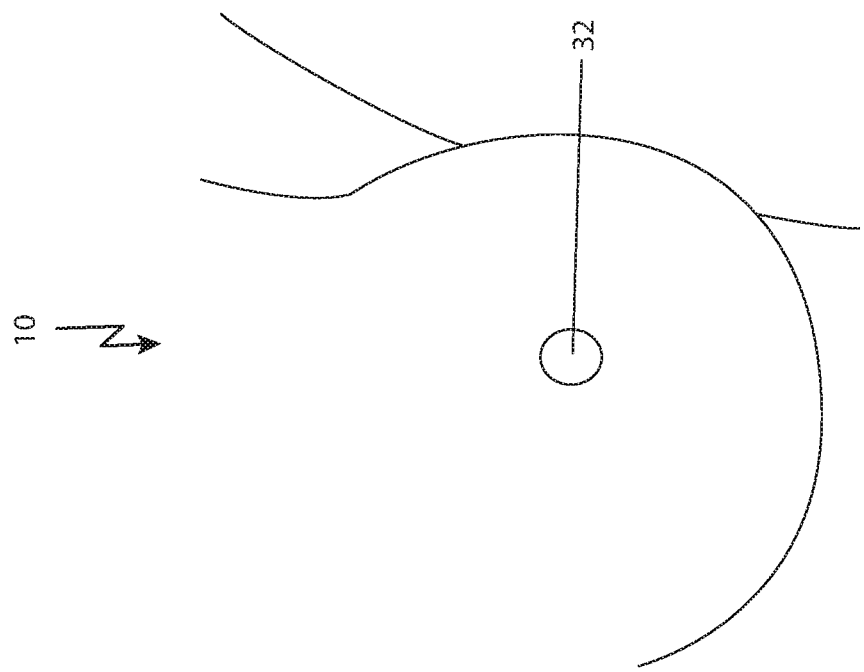
FIG. 11b illustrates a front perspective view of a breast after reconstruction using devices as taught herein, in accordance with one embodiment.
Figure 11A:
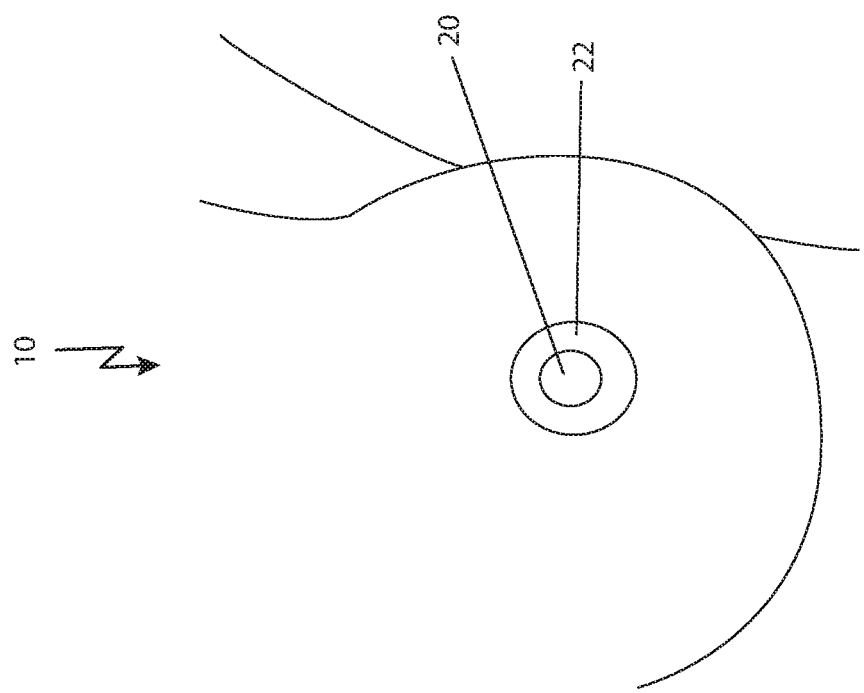
FIG. 11a illustrates a front perspective view of a breast before mastectomy.

FIG. 11a illustrates a front perspective view of a breast 10 before mastectomy. As shown, the breast 10 includes a nipple 20 and areola 22, the nipple 20 protruding from the breast mound. FIG. 11b illustrates a front perspective view of a breast 10 after reconstruction using devices as taught herein. As shown, the breast 10 includes a nipple like protrusion 32 protruding from the breast mound.

The expansion implant and the reconstruction implant may be formed or manufactured using the same or substantially similar mold or die. As will be apparent to one skilled in the art, the shape, size and/or form of an empty expander formed in this manner will be substantially similar to that of the desired final shape, size and/or form of the expander when filled with the biocompatible fluid. The expansion implant and the reconstruction implant may have complementary configurations. Accordingly, in some embodiments, one of the expansion implant or the reconstruction implant may be used as a mold or die to form the other.

In another embodiment, the expansion implant may be filled with a biocompatible substance after the biocompatible fluid is removed and may itself be used as a reconstruction implant.

In an alternative embodiment, after removal of the expansion implant, the pocket or void formed in the breast mound by the expansion implant may be filled with a biocompatible substance and a reconstruction implant may not be used.

In view thereof, modified and/or alternate structures or configurations providing structures and/or functionalities similar to the non-limiting exemplary embodiments disclosed herein may become apparent or obvious to a person of ordinary skills. Accordingly, any and all variants of the non-limiting exemplary embodiments disclosed herein are considered as being within the metes and bounds of the instant disclosure.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

Additionally, as used herein, the phrase "at least one of [X] and [Y]," where X and Y are different components that may be included in an embodiment of the present disclosure, means that the embodiment could include component X without component Y, the embodiment could include the component Y without component X, or the embodiment could include both components X and Y. Similarly, when used with respect to three or more components, such as "at least one of [X], [Y], and [Z]," the phrase means that the embodiment could include any one of the three or more components, any combination or sub-combination of any of the components, or all of the components.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A system for breast reconstruction comprising:
   an expansion implant for creating a breast mound, the expansion implant comprising:
      an expander portion configured to receive a fluid and expand upon receiving the fluid; and
      a nub comprising a substantially rigid protrusion, the nub extending outwardly from the expander portion when the expander is in an expanded configuration, the nub having a size and shape mimicking extension of a nipple from breast tissue;
      wherein, when the expansion implant is implanted and expanded, the nub creates a nipple-like protrusion in the breast mound; and
   a reconstruction implant comprising:
      a breast portion; and
      a nipple portion extending outwardly from the breast portion.

2. The system of claim 1, wherein the expansion implant further comprises a port for accessing an interior of the expander portion.

3. The system of claim 1, wherein the expander portion has a round shape.

4. The system of claim 1, wherein the expansion implant and the reconstruction implant have complimentary shapes.

5. The system of claim 4, wherein the expansion implant and the reconstruction implant have anatomical shapes.

6. The system of claim 1, wherein the nub does not extend outwardly from the expander portion when the expander portion does not contain fluid.

7. The system of claim 1, wherein the nub is integral with the expander portion.

8. The system of claim 1, wherein the nub is coupled to the expander portion.

9. The system of claim 1, wherein an outward facing surface of the breast portion is textured.

10. The system of claim 1, wherein the nipple portion is integral with the breast portion.

11. The system of claim 1, wherein the nipple portion is coupled the breast portion.

12. An expansion implant for creating a breast mound, the expansion implant comprising:
   an expander portion configured to receive a fluid and expand upon receiving the fluid;
   a nub comprising a substantially rigid protrusion, the nub extending outwardly from the expander portion when the expander is in an expanded configuration, the nub having a size and shape mimicking extension of a nipple from breast tissue; and
   a port for accessing an interior of the expander portion;
   wherein, when the expansion implant is implanted and expanded, the nub creates a nipple-like protrusion in the breast mound.

13. The implant of claim 12, wherein the expander portion has a round shape.

14. The implant of claim 12, wherein the nub does not extend outwardly from the expander portion when the expander portion does not contain fluid.

15. The implant of claim 12, wherein the nub is integral with the expander portion.

16. The implant of claim 12, wherein the nub is coupled to the expander portion.

17. The implant of claim 12, wherein the nub forms a nipple cavity in a breast region of a human when implanted.

18. A method for reconstruction of a breast comprising:
   implanting an expansion implant in a breast region, the expansion implant being configured for creating a breast mound and comprising:
      an expander portion configured to receive a fluid and expand upon receiving the fluid;
      a nub comprising a substantially rigid protrusion, the nub extending outwardly from the expander portion when the expander is in an expanded configuration, the nub having a size and shape mimicking extension of a nipple from breast tissue; and
      a port for accessing an interior of the expander portion;
      wherein, when the expansion implant is implanted and expanded, the nub creates a nipple-like protrusion in the breast mound
   expanding the expander portion by injecting fluid through the port and into the expander portion, wherein expansion of the expander portion forces the nub to push outwardly and create the nipple-like protrusion;
   removing the expansion implant to leave a cavity in the breast region, the cavity including a nipple cavity;
   implanting a reconstruction implant into the cavity, the reconstruction implant comprising:
      a breast portion; and
      a nipple portion extending outwardly from the breast portion;
   wherein implanting the reconstruction implant includes positioning the nipple portion into the nipple cavity.

* * * * *